US008487089B2

(12) United States Patent
Boström et al.

(10) Patent No.: US 8,487,089 B2
(45) Date of Patent: Jul. 16, 2013

(54) ASSOCIATIVE WATER-SOLUBLE CELLULOSE ETHERS

(75) Inventors: Peter Boström, Ytterby (SE); Leif Karlson, Stenungsund (SE)

(73) Assignee: Akzo Nobel N.V., Arnhem (NL)

( * ) Notice: Subject to any disclaimer, the term of this patent is extended or adjusted under 35 U.S.C. 154(b) by 582 days.

(21) Appl. No.: 10/582,308

(22) PCT Filed: Dec. 15, 2004

(86) PCT No.: PCT/EP2004/014376
§ 371 (c)(1),
(2), (4) Date: Jul. 19, 2006

(87) PCT Pub. No.: WO2005/058971
PCT Pub. Date: Jun. 30, 2005

(65) Prior Publication Data
US 2007/0059267 A1    Mar. 15, 2007

(30) Foreign Application Priority Data

Dec. 15, 2003    (SE) ...................................... 0303352

(51) Int. Cl.
*C08B 11/00*    (2006.01)
*C08B 11/193*    (2006.01)

(52) U.S. Cl.
USPC ................................. 536/84; 536/90; 536/91

(58) Field of Classification Search
None
See application file for complete search history.

(56) References Cited

U.S. PATENT DOCUMENTS

| | | | | |
|---|---|---|---|---|
| 4,228,277 A | | 10/1980 | Landoll | 536/90 |
| 4,826,970 A | * | 5/1989 | Reid et al. | 536/66 |
| 4,904,772 A | * | 2/1990 | Sau | 536/90 |
| 5,140,099 A | | 8/1992 | Bostrom et al. | 536/91 |
| 5,521,234 A | | 5/1996 | Brown et al. | 524/44 |
| 6,068,697 A | * | 5/2000 | Yamamuro et al. | 106/804 |
| 6,627,751 B1 | | 9/2003 | Batelaan et al. | 536/84 |

FOREIGN PATENT DOCUMENTS

| | | |
|---|---|---|
| EP | 0566911 A1 | 10/1993 |
| EP | 1035134 A1 | 9/2000 |
| JP | 3-12401 | 1/1991 |
| JP | 2002-522569 | 7/2002 |
| JP | 2002-370963 | 12/2002 |
| JP | 2003-530441 | 10/2003 |
| WO | WO 00/08058 | 2/2000 |
| WO | WO 00/35957 A1 | 6/2000 |
| WO | WO 00/52059 | 9/2000 |
| WO | WO 03/048211 A1 | 6/2003 |

OTHER PUBLICATIONS

JP 2002-370963A, 2002, machine translation.*
JP 03-012401, 2003, translation.*
Immergut et al. Industrial and Engineering Chemistry, Nov. 1953, pp. 2483-2490.*
International Search Report for International Application No. PCT/EP2004/014376, Apr. 4, 2005.
Landoll et al., "Nonionic Polymer Surfactants," Journal of Polymer Science: Polymer Chemistry Edition, vol. 20 pp. 443-455 (1982).
Cheng et al., "Characteristics of Carboxymethyl Cellulose Synthesized in Two-Phase Medium $C_6H_6$-$C_2H_5OH$.I. Distribution of Substituent Groups in the Anhydroglucose Unit," Journal of Applied Polymer Science, vol. 61, pp. 1831-1838 (1996).
Stead et al., "A Modified Method for the Analysis of Oxyethylene/Oxypropylene Copolymers by Chemical Fission and Gas Chromatography," J. Chromatog, vol. 42, pp. 470-475 (1969).
Hodges et al., "Determiniation of Alkoxyl Substitution in Cellulose Ethers by Zeisel-Gas Chromatography," Analytical Chemistry, vol. 51, No. 51, pp. 2172-2176 (1979).
English Patent Abstract for Japanese Publication No. 03-012401 1991.
English Patent Abstract for Japanese Publication No. 2002-370963.
Klug et al., "Some properties of water-soluble hydroxyalkyl celluloses and their derivatives," J. Polymer Sc.: Part C, No. 3, pp. 491-508 (1971).
Landoll, "Nonionic Polymer Surfactants," Journal of Polymer Science: Polymer Chemistry edition, vol. 20, pp. 443-455 (1982).
Klug, "Hydroxyethyl ethers of cellulose and their analytical determination," Hercules Powder Company, p. 315-317 1963.
Figini, "Significance of the intrinsic viscosity ration of undubstituted and nitrated cellulose in different solvents," vol. 72, pp. 161-171 (1978).
Gelman et al., "Viscosity studies of hydrophobically modified (Hydroxyethyl) cellulose," Hercules, Inc., Advances in Chemistry Series 213, pp. 101-110 (1986).
English Translation of Japanese Office Action mailed Mar. 8, 2011.
Sangelose, Daido Chemical Industry Co., Ltd., May 2003.
Huckfeldt et al., "Die Temming-Methode zur Viskositatsbestimmung an linters-cellulosen," pp. 315-325 (1995).
English Machine Translation of Huckfeldt et al., "Die Temming-Methode zur Viskositatsbestimmung an linters-cellulosen," pages 315-325 (1995).
Schulz et al., "Eine Gleichung zur Berechnung der Viscoitatszahl fur sehr kleine Konzentrationen," Journal fur pracktische Chemie N.F. Band 158, pp. 130-135 (1941).
English Machine Translation of Schulz et al., "Eine Gleichung zur Berechnung der Viscoitatszahl . . . ," Journal fur pracktische Chemie N.F. Band 158, pp. 130-135 (1941).
Schulz et al., "Molekulargewitchtsbestimmungen an einer Reihe von Polymethacrylsauremethylestern nach . . . ," Journal fur pracktische Chemie N.F. Band 158, pp. 136-162 (1941).

(Continued)

*Primary Examiner* — Layla Bland
(74) *Attorney, Agent, or Firm* — Robert C. Morriss

(57) ABSTRACT

The present invention relates to a water-soluble associative cellulose ether having a DP viscosity from 250 to 20,000 mPa·s, measured at a concentration of 1% by weight, and a molecular substitution, MS, from 0.0001 to 0.005 of a hydrophobic substituent containing an unsubstituted or substituted hydrocarbon group of 8-24 carbon atoms. The cellulose ether has a good thickening effect and advantageous application properties at low contents and can be used in an aqueous decorative paint composition, an aqueous paper coating composition, an aqueous organic filler composition, an aqueous cement slurry, an aqueous detergent composition or an aqueous personal care formulation.

11 Claims, No Drawings

OTHER PUBLICATIONS

English Machine Translation of Schulz et al., "Molekulargewitchtsbestimmungen an einer Reihe von . . . ," Journal fur pracktische Chemie N.F. Band 158, pp. 136-162 (1941).

Karlson, Leif, "Hydrophobically Modified Polymers Rheology and Molecular Associations, " Thesis Physical Chemistry 1, Lund University, 2002, 131 pages.

Klug et al., "Some properties of water-soluble hydroxyalkyl celluloses and their derivatives," J. Polymer Sc.: Part C, No. 36, pp. 491-508 (1971).

Marx-Figini, "Significance of the intrinsic viscosity ration of undubstituted and nitrated cellulose in different solvents" Die Angewandte Makromolekulare Chemie 72(1978)161-171.

Huckfeldt et al., "Die Temming-Methode zur Viskositatsbestimmung an linters-cellulosen," Das Paper, vol. 49, Issue 6, pp. 315-325 (1995).

\* cited by examiner

ASSOCIATIVE WATER-SOLUBLE CELLULOSE ETHERS

This case was filed under the Patent Cooperation Treaty on Dec. 15, 2004 and claims priority of Swedish priority application serial No. 0303352-9, filed on Dec. 15, 2003.

The present invention relates to an associative water-soluble cellulose ether having a high average degree of polymerization (DP) and a low substitution of hydrophobic substituents containing a hydrocarbon group of 8-24 carbon atoms. At low temperatures, the cellulose ether has a good thickening effect and advantageous application properties, especially in aqueous dispersions, such as aqueous compositions containing water-insoluble binders.

Today water-soluble cellulose ethers, for instance cellulose ethers having a low DP, are frequently used as a thickening and rheology agent in aqueous dispersions. Examples of such dispersions are decorative paint compositions, paper coating compositions, joint fillers, and cement compositions. However, the cellulose ethers with a low DP have to be added in a high amount in order to impart good rheology properties. Since the cellulose ethers are water-soluble, there is a general desire for example in decorative paint compositions to use as little as possible of the cellulose ethers to minimize the water sensibility of the dispersions when dried.

A reduction of the amount of cellulose ethers needed can be obtained by using cellulose ethers having a high DP. However, even if cellulose ethers with a high DP have a better thickening effect and water retention, other rheology properties such as hiding power and spatter are not satisfactory. A method of reducing spatter is to use a large amount of a cellulose ether having a low DP.

By using associative cellulose ethers, i.e. cellulose ethers with a substituent containing a large hydrocarbon group having more than about 10 carbon atoms and with a very low DP, the spatter can be essentially reduced. The associative cellulose ethers of low DP also positively affect the hiding power depending on a high ICI viscosity and good levelling, but this demands a high amount of addition.

In joint fillers, cellulose ethers of high DP can be used in small amounts as a thickening and water retention agent. Unfortunately, the water retention agent also results in increased sagging when the joint filler is applied on a vertical surface. This effect is often counteracted by the addition of different clays.

It has now been found that when added in small quantities, associative water-soluble cellulose ethers having a high DP and a low degree of substitution of hydrophobic substituents containing hydrocarbon groups of 8-24 carbon atoms impart unique properties to aqueous dispersions, such as a high water retention and thickening effect, low spatter and sagging and/or a good hiding power and levelling effect.

The associative water-soluble cellulose ethers according to the invention have a DP viscosity, expressed in terms of viscosity and measured at a concentration of 1% by weight at 20° C., from 250 to 20,000 mPa·s, preferably from 1,000 to 15,000 mPa·s, and most preferably from 2,000 to 15,000 mPa·s, and an average molecular substitution (MS) from 0.0001 to 0.005, preferably from 0.0002 to 0.0035, and most preferably from 0.0003 to 0.0028, of a hydrophobic substituent (MS hydrofobe) containing an unsubstituted or substituted hydrocarbon group of 8-24 carbon atoms, preferably from 10 to 20 carbon atoms. The unsubstituted hydrocarbon group can be an aliphatic group or an aromatic group, such as nonylphenyl or octylphenyl. The substituted hydrocarbon group can contain a hydroxyl group or a fluoride group.

The DP viscosity can be measured using a conventional rheometer, such as a Rheolica Controll Stress rheometer, using a 40 mm, 1° cone and plate measurement system, at a shear stress of 0.5 Pa and a temperature of 20° C. The DP viscosity, as used throughout this document, is determined by dissolving the polymer in a solvent system consisting of 20% by weight of di(ethylene glycol)butyl ether and 80% by weight of water at 20° C. The viscosities obtained were then divided by a factor 2.7, in order to compensate for the higher viscosities obtained in an aqueous solution containing 20% by weight of poly(ethylene glycol)butyl ether in comparison with the viscosities obtained in pure water. The molecular substitution, MS, of the hydrophobic groups was determined by the method described by Landoll, L. M., *J Polym. Sci., Part A: Polymer Chem.*, 1982, Vol. 20, pages 433, 443-455.

The associative water-soluble cellulose ether according to the invention preferably has an average degree of polymerization (DP) of at least 800, preferably at least 850, and most preferably at least 900, and generally at most 8,000, preferably at most 7,500, and most preferably at most 7,000. The DP can be derived from the intrinsic viscosity of the cellulose ether, as is known in the art.

According to the invention, the cellulose ethers of the invention are nonionic or ionic and suitably have a hydrophobic substituent of the formula

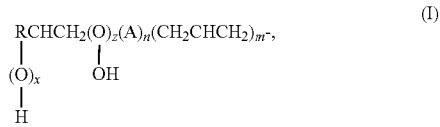

wherein A is an alkyleneoxy group with 2-3 carbon atoms, x, z, and m are a number 0 or 1, n is a number from 0-7, with the proviso that when x and z are both 0, then n and m are both 0, and R represents a hydrocarbon group of 6 to 22, preferably from 8-18, carbon atoms. When x is 1, z, n, and m suitably are 0, and when z is 1, x suitably is 0 and m is 1. The groups $RCH_2CH_2$ and $RCH(OH)CH_2$ represent the unsubstituted hydrocarbon group and the substituted hydrocarbon group containing 8-24 carbon atoms mentioned above.

The hydrocarbon group $RCH_2CH_2$ can be a straight aliphatic group, such as n-octyl, n-nonyl, n-decyl, n-dodecyl, n-tetradecyl, n-hexadecyl, n-octadecyl, n-eicosyl, and n-docosyl, the corresponding unsaturated aliphatic compounds, and branched aliphatic groups containing 8-24 carbon atoms and at least one methyl or ethyl branch. The substituted hydrocarbon group $RCH(OH)CH_2$ can be derived from α-epoxides with 10-24 carbon atoms obtained by epoxidation of α-unsaturated aliphatic compounds with 10-24 carbon atoms.

Examples of suitable hydrophobic substituents are

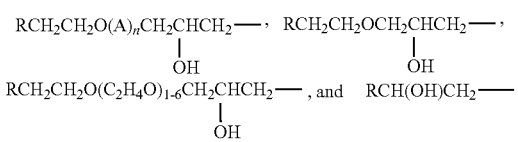

wherein A, R, and n have the meanings mentioned in the explanation of formula I above.

Besides the hydrophobic substituents, the cellulose ether according to the invention contains one or more substituents selected from the group consisting of hydroxyethyl, hydroxypropyl, methyl, ethyl, carboxymethyl, and a cationic substituent having a primary, secondary, tertiary or quaternary ammonium group. If the cellulose ether is a nonionic cellulose ether, the cellulose ether has a MS hydroxyethyl from 0.2 to 4.5. Suitably the nonionic cellulose ether has a cloud point temperature from 50 to 90° C., preferably from 55 to 80° C. Such a nonionic cellulose ether normally contains methyl and/or ethyl substituents in addition to the hydroxyethyl and the hydrophobic substituents. A well-adapted cloud point temperature may have a positive influence on the rheology properties and will facilitate the cleaning and drying of the cellulose ether.

The cellulose ethers of the invention can also be anionic and have an average degree of substitution of carboxymethyl groups (DS carboxymethyl) from 0.3 to 1.4, preferably from 0.6 to 1.0. The DS carboxymethyl is determined by using a 300 mHz Bruker NMR spectrometer as specified by F Cheng et al. in *I. Applied Pol. Sci.*, Vol 61, 1831-1838 (1996). In addition to the carboxymethyl substituents, the anionic cellulose ether can also be substituted with hydroxyethyl, hydroxypropyl, methyl and/or ethyl. The cationic cellulose ethers normally contain a substituent containing an ammonium ion, which can be primary, secondary, tertiary or quaternary. The MS ammonium typically is 0.01-1.0. The quaternary substituents are normally preferred. The amounts of $N^+$ in cationic cellulose ethers are determined by Kjeldahl analysis. Preferably, the cationic cellulose ethers contain hydroxyethyl substituents but also substituents selected from the group consisting of hydroxypropyl, methyl, and ethyl can be present.

The cellulose ethers of the present invention can be prepared by reaction steps known per se. Thus, a water-soluble cellulose ether having a DP viscosity from about 250 to 20,000 mPa·s can be further reacted under alkaline conditions with a reactant of the formula

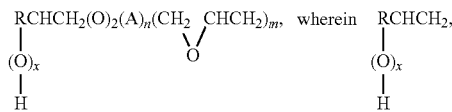

A, z, n, and m have the meanings mentioned above, in a suitable reaction medium. After the reaction the reaction medium is removed and the cellulose ether obtained may be washed with water and/or organic solvents, such as alcohols, to remove by-products formed during the reaction.

Because they have unique rheological properties and a high thickening ability at a low amount, the cellulose ethers of the present invention can be advantageously used in many formulations within several application fields.

The formulations may have the form of solutions, emulsions, dispersions or suspensions. Typical application areas are aqueous decorative paint compositions, such as latex paints; aqueous organic filler compositions; aqueous personal care formulations, such as shampoos, aqueous conditioners, and cosmetics; aqueous detergent compositions, such as hard surface cleaners and compositions for laundry; aqueous cement slurries, and aqueous paper coating compositions, such as coating slips.

In aqueous paper coating compositions, the cellulose ethers can be nonionic or anionic or a combination thereof. Suitable compositions are for example aqueous coating slips containing a latex and calcium carbonate and a cellulose ether of the invention as a thickening agent.

The cationic cellulose ethers can advantageously be used in aqueous personal care products, since these ethers have excellent thickening and antistatic properties, as well as an ability to adhere to skin and hair.

The cellulose ethers are also well suited for use in water borne flat, semi-flat, semi-gloss, and gloss paint compositions, not only as thickeners but also as stabilizers. The amounts of cellulose ethers added vary depending on both the ingredients of the paint compositions and the substitution and the viscosity of the cellulose ethers, but normally the addition is 0.1 to 1.2% by weight of the paint compositions. The nonionic and anionic cellulose ethers may well be used in paint formulations containing emulsion binders such as alkyd resins and latex binders, such as polyvinyl acetate, copolymers of vinyl acetate and acrylate, copolymers of vinyl acetate and ethylene, copolymers of vinyl acetate, ethylene, and vinyl chloride, and copolymers of styrene and acrylate. The latex binders are often stabilized with anionic surfactants.

The present invention is further illustrated by the following Examples.

EXAMPLE 1

One mole of an ethylene oxide adduct of the formula $R_1O(C_2H_4O)_2H$, wherein $R_1$ is a blend of dodecyl and tetradecyl, and one mole of epichlorohydrin were reacted in the presence of tin tetrachloride at 70° C. After the reaction a 30% by weight solution of sodium hydroxide in water was added to the reaction mixture at 80° C. and a glycidylether of the formula

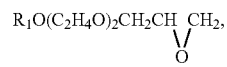

wherein $R_1$ has the meaning mentioned above, was obtained and separated from the water phase.

A powder of dissolved wood pulp expected to give a cellulose ether of DP viscosity of about 10,000 mPa·s was added to the reactor in an amount of 100 parts. The air in the reactor was evacuated and replaced by nitrogen, sodium hydroxide in an amount of 70 parts by weight as a 50% by weight water solution, ethyl chloride (150 parts), ethylene oxide (84 parts), and glycidyl ether (2.2 parts).

The reactor temperature was increased to 55° C. and the reactor held at this temperature for 50 minutes, after which the reactor temperature was increased to 105° C. and held there for 50 minutes. The cellulose ether obtained was washed with boiling water and neutralized with acetic acid. The cellulose ether had a MS hydroxyethyl of 2.1, a DS ethyl of 0.9, a MS hydrophobe of 0.0025, and a cloud point temperature of 59° C. The cloud point temperature, $T_{cp}$, at which the polymer solutions (at a concentration of 1 wt %) phase separates, was determined by visual detection. The solutions were kept in spectrophotometer cuvettes which were immersed in a thermostatted water bath. The temperature was increased in steps of 2° C. After each change of the temperature the samples were left to equilibrate for 20 minutes before observation. $T_{cp}$ is defined as the temperature at which the 1 wt % cellulose ether solution first becomes hazy.

The substitution of ethyl and hydroxyethyl was determined by cleaving the ethoxy and hydroxyethoxy groups with hydrobromic acid in acetic acid, the ethyl and hydroxyethyl groups forming ethyl bromide and 1,2-dibromoethane. The amounts of these bromides were then determined by gas chromatography. See also Hodges, K. L., *Analytical Chemistry*, Vol 51 (1979), p 2172 and Stead Hindley, *J Chromatog.* (1969), pp 470-475.

EXAMPLE 2

Example 1 was repeated, but a dissolving wood pulp expected to give a cellulose ether of a DP viscosity of about 6,000 mPa·s was used. The cellulose ether had a MS hydroxyethyl of 2.1, a DS ethyl of 0.8, a MS hydrophobe of 0.0026, and a cloud point temperature of 61° C.

EXAMPLE 3

Example 2 was repeated, but the amount of glycidyl ether was 2.0 parts by weight. The cellulose ether had a MS hydroxyethyl of 2.1, a DS ethyl of 0.8, a MS hydrophobe of 0.0018, and a cloud point temperature of 64° C.

EXAMPLE 4

Example 1 was repeated, but a dissolving wood pulp expected to give a cellulose ether of a DP viscosity of about 15,000 mPa·s was used and the alkyl groups in the glycidyl ether were replaced by a blend of hexadecyl and octadecyl. This glycidyl ether was added in 0.3 parts by weight. The cellulose ether had a MS hydroxyethyl of 2.1, a DS ethyl of 0.9, a MS hydrophobe of 0.0004, and a cloud point temperature of 65° C.

EXAMPLE 5

Example 4 was repeated, but the amount of glycidyl ether was 0.6 parts by weight. The cellulose ether had a MS hydroxyethyl of 2.1, a DS ethyl of 0.8, a MS hydrophobe of 0.0007, and a cloud point temperature of 65° C.

EXAMPLE 6

Example 4 was repeated, but the amount of glycidyl ether was 1.2 parts by weight. The cellulose ether had a MS hydroxyethyl of 2.1, a DS ethyl of 0,8, a MS hydrophobe of 0.0012, and a cloud point temperature of 65° C.

EXAMPLE 7

A solution of 81 g of sodium hydroxide in 20 g of water was added with stirring to a mixture of 150 g of linter cellulose and 40 g of water under a nitrogen atmosphere at 20° C., followed by the addition of a solution of 103.9 g of chloroacetic acid in 20 g of water, 60 g of n-butyl glycidyl ether, and 16 g of a glycidyl ether of the formula

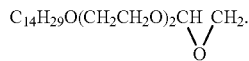

The mixture obtained was heated to 85° C. and was held at this temperature for 26 hours and then cooled and neutralized with acetic acid. The crude cellulose ether obtained was washed three times each with an aqueous solution of 65% by weight of ethanol, an aqueous solution with 80% by weight of ethanol, and a solution containing 80% by weight of ethanol and 20% by weight acetone and then dried. The cellulose ether had a DS carboxymethyl of 0.9, a MS n-butyl glycidyl of 0.2, and a MS hydrophobe of 0.004. The substitution of the butyl glycidyl ether group was determined by using a NMR spectrometer in a manner similar to the determination of the carboxymethyl group.

EXAMPLE 8

The cellulose ethers prepared in Examples 1-7 as well as some cellulose ethers for comparison were tested with regard to the viscosity in water and the DP viscosity. The concentration of the cellulose ethers was 1% by weight. The cellulose ethers used in the comparisons are shown in Table 1 below. The viscosity measurements were performed in a Rheolica Controll Stress rheometer, equipped with a 40 mm, 1° cone and plate measurement system, at 0.5 Pa and 20° C. The viscosities obtained are shown in Table 2 below.

TABLE 1

Cellulose ethers used in comparison tests

| Cellulose ethers | MS hydroxyethyl | DS ethyl | MS hydrophobe | Hydrocarbon group | Flocculation temp, ° C. |
|---|---|---|---|---|---|
| A | 2.2 | 0.9 | — | — | 68 |
| B | 2.5 | 0.8 | — | — | 69 |
| C | 2.2 | 0.9 | — | — | 68 |
| D | 2.0 | 0.9 | — | — | 65 |
| E | 4.0 | — | 0.013 | $C_{16}C_{18}$ | — |
| F | 2.1 | 0.8 | 0.010 | $C_{12}C_{14}$ | 47 |

TABLE 2

Viscosities and DP viscosities of the cellulose ethers in Examples 1-6 and the comparison cellulose ethers A-F

| Cellulose ether | MS hydrophobe | Hydrocarbon group | Viscosity in water mPa·s | DP viscosity mPa·s |
|---|---|---|---|---|
| A | — | — | 17,600 | 14,900 |
| B | — | — | 11,200 | 9,700 |
| C | — | — | 1,120 | 1,050 |
| D | — | — | 140 | 130 |
| E | 0.013 | $C_{16-18}$ | 19,200 | 100 |
| F | 0.010 | $C_{12-14}$ | 99,000 | 1,450 |
| Ex 1 | 0.0025 | $C_{12-14}$ | 46,200 | 8,500 |
| Ex 2 | 0.0026 | $C_{12-14}$ | 10,300 | 4,770 |
| Ex 3 | 0.0018 | $C_{12-14}$ | 9,800 | 5,700 |
| Ex 4 | 0.0004 | $C_{16-18}$ | 13,900 | 10,400 |
| Ex 5 | 0.0007 | $C_{16-18}$ | 17,000 | 11,700 |
| Ex 6 | 0.0012 | $C_{16-18}$ | 45,500 | 13,864 |
| Ex 7 | 0.004 | $C_{14}$ | 4,330 | 1,010 |

The results show that even a low MS of the hydrophobe modifying group, for example 0.0004, gives an essential contribution to the viscosity.

EXAMPLES 9 AND 10

In these examples different cellulose ethers were tested as thickening agents in two paint formulations shown in Table 3 below. The amounts of the cellulose ethers were adapted in such a manner that the paint formulations obtained a Stormer viscosity of 105 KU.

TABLE 3

| Components | Formulation 1 % by weight | Formulation 2 % by weight |
|---|---|---|
| Latex | | |
| Styrene-acrylate (Acronal 290 D) | 14.0 | — |
| Vinylacetate-ethene-vinylchloride (Mowilith DM 122) | — | 6.0 |

TABLE 3-continued

| Components | Formulation 1 % by weight | Formulation 2 % by weight |
|---|---|---|
| Water | 38.7-x | 45.9-x |
| Cellulose ether tested | x | x |
| Defoamer | 0.2 | 0.4 |
| Bactericide | 0.1 | 0.1 |
| Dispersing agent | 0.4 | 0.5 |
| Propylene glycol | 1.5 | — |
| Titanium dioxide | 6.0 | 3.0 |
| Calcium carbonate | 37.5 | 34.0 |
| Microtalc | 1.3 | 10.0 |

The paint formulations were tested with regard to their ICI viscosities, levelling, and spatter. The effects on levelling and spatter were visually determined by a test panel according to a scale from 1 to 10. In the scale for levelling 1 stands for very poor levelling and 10 for perfect levelling, while in the scale for spatter, 1 stands for a high degree of spatter and 10 for no spatter at all. The following results were obtained.

TABLE 4

ICI viscosity, levelling and spatter of formulations based on styrene-acrylate latex

| Cellulose ether | | | | |
|---|---|---|---|---|
| Type | Amount % by weight | ICI viscosity Pa·s | Levelling | Spatter |
| A | 0.50 | 1.2 | 3 | 3 |
| B | 0.55 | 1.2 | 3 | 3 |
| C | 0.70 | 1.0 | 3 | 3 |
| D | 0.85 | 1.6 | 4 | 4 |
| E | 0.51 | 1.0 | 3 | 8 |
| F | 0.44 | 1.1 | 1 | 6 |
| Ex 1 | 0.30 | 1.2 | 4 | 6 |
| Ex 2 | 0.35 | 1.1 | 4 | 6 |
| Ex 3 | 0.45 | 1.3 | 3 | 5 |
| Ex 4 | 0.43 | 1.1 | 3 | 5 |
| Ex 5 | 0.33 | 1.1 | 4 | 5 |
| Ex 6 | 0.24 | 0.9 | 5 | 6 |
| Ex 7 | 0.40 | 1.2 | 4 | 6 |

TABLE 5

ICI viscosity, levelling, and spatter of paint formulations based on vinylacetate-ethylene-vinylchloride latex

| Cellulose ether | | | | |
|---|---|---|---|---|
| Type | Amount % by weight | ICI viscosity Pa·s | Levelling | Spatter |
| A | 0.43 | 1.0 | 9 | 3 |
| B | 0.50 | 1.1 | 9 | 3 |
| C | 0.65 | 1.5 | 9 | 4 |
| D | 0.85 | 1.8 | 9 | 4 |
| E | 0.52 | 1.2 | 7 | 6 |
| F | 0.65 | 1.6 | 7 | 6 |
| Ex 1 | 0.35 | 1.4 | 9 | 5 |
| Ex 2 | 0.36 | 1.4 | 9 | 6 |
| Ex 3 | 0.41 | 1.4 | 9 | 5 |
| Ex 4 | 0.40 | 1.4 | 10 | 4 |
| Ex 5 | 0.35 | 1.3 | 10 | 5 |
| Ex 6 | 0.30 | 1.3 | 10 | 6 |

The results show that the cellulose ethers of the invention can be used in lower amounts and/or with lower amounts of the hydrophobic substituents than the comparison cellulose ethers and still have at least equal and in most cases even better ICI viscosities, spatter, and levelling.

EXAMPLE 11

A high-viscous filler was prepared by mixing the following ingredients:

| Ingredient | Parts by weight |
|---|---|
| Carbonate of magnesium and calcium | 946.5 |
| Chalk hydrate | 10 |
| Thickener in accordance with Table 6 below | 5 |
| Vinylacetate-ethene-vinylchloride (Mowilith DM 122) | 30 |
| Bactericide | 1 |
| Dispersing agent (polyacrylic acids) | 0.5 |
| Defoamer | 2 |
| Water | 350 |

The flowability of the fillers was tested by means of the ring test. The following results were obtained.

TABLE 6

Flow properties of fillers containing different cellulose ethers

| Cellulose ether | Ring test, mm flow |
|---|---|
| B | 68.5 |
| F | 65 |
| Ex 1 | 37 |
| Ex 2 | 49 |
| Ex 7 | 45 |

From the results it is evident that the flow of the filler compositions according to the invention is lower than the flow of the compositions containing the comparison cellulose ethers.

The invention claimed is:

1. A method of thickening an aqueous composition which comprises adding to said aqueous composition at least one associative water-soluble nonionic cellulose ether, wherein said ether has a DP viscosity, measured at a concentration of 1% by weight at 20° C., from 1000 mPa·s to 15,000 mPa·s and an average MS from 0.0001 to 0.005 of hydrophobic substituents containing an unsubstituted or substituted hydrocarbon group of 8-24 carbon atoms.

2. The method of claim 1, wherein the average MS of the cellulose ether is from 0.0003 to 0.0028.

3. The method of claim 1 wherein the cellulose ether contains substituents selected from the group consisting of hydroxyethyl, hydroxypropyl, methyl, ethyl and mixtures thereof.

4. The method of claim 1 wherein the cellulose ether has a MS hydroxyethyl of 0.8-4.5.

5. The method of claim 4 wherein the cellulose ether contains methyl substituents or ethyl substituents or a mixture thereof.

6. The method of claim 1 wherein the cellulose ether has a cloud point temperature from 50° C. to 90° C.

7. The method of claim 1 wherein said aqueous composition is selected from the group consisting of an aqueous decorative paint composition, an aqueous paper coating composition, an aqueous organic filler composition, an aqueous cement slurry, an aqueous detergent composition and aqueous personal care formulation.

8. The method of claim 1 wherein the hydrophobic substituent of the cellulose ether has the formula

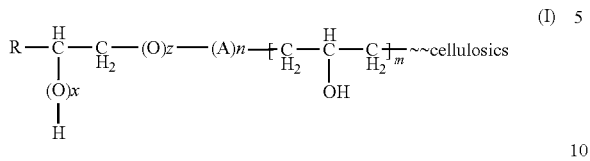

(I)

wherein A is an alkyleneoxy group with 2-3 carbon atoms, x, z, and m are a number 0 or 1, n is a number from 0-7, with the proviso that when x and z are both 0, then n and m are both 0, and R represents a hydrocarbon group of 6-22 carbon atoms.

9. The method of claim 8 wherein when z is 1, x is 0 and m is 1.

10. A composition selected from the group consisting of aqueous decorative paint composition, an aqueous paper coating composition, an aqueous organic filler composition, an aqueous cement slurry, an aqueous detergent composition and aqueous personal care formulation, wherein said composition comprises at least one associative water-soluble nonionic cellulose ether, wherein said ether has a DP viscosity, measured at a concentration of 1% by weight at 20° C., from 1000 mP·s to 15,000 mPa·s and an average MS from 0.0001 to 0.005 of hydrophobic substituents containing an unsubstituted or substituted hydrocarbon group of 8-24 carbon atoms.

11. The composition of claim 10 wherein said composition is a paint composition that comprises an alkyd emulsion or latex.

* * * * *